United States Patent
Bratovanov et al.

(10) Patent No.: US 8,143,400 B2
(45) Date of Patent: Mar. 27, 2012

(54) PROCESS FOR THE PREPARATION AND PURIFICATION OF CIS-2-METHYLSPIRO (1,3-OXATHIOLANE-5,3')QUINICLIDINE HYDROCHLORIDE

(75) Inventors: Svetoslav S. Bratovanov, Ancaster (CA); Elena Bejan, Brantford (CA); David A. Stradiotto, Brantford (CA); Abbulu Kante, Brantford (CA); Zhi-Xian Wang, Tianjin (CN); Stephen E. Horne, Burlington (CA)

(73) Assignee: Apotex Pharmachem Inc., Brantford (CA)

( * ) Notice: Subject to any disclaimer, the term of this patent is extended or adjusted under 35 U.S.C. 154(b) by 980 days.

(21) Appl. No.: 12/007,394

(22) Filed: Jan. 10, 2008

(65) Prior Publication Data

US 2009/0182146 A1    Jul. 16, 2009

(51) Int. Cl.
*C07D 401/14*    (2006.01)
(52) U.S. Cl. ........................................... 546/18; 546/19
(58) Field of Classification Search .................... 546/18, 546/19
See application file for complete search history.

(56) References Cited

U.S. PATENT DOCUMENTS

| | | |
|---|---|---|
| 4,855,290 A | 8/1989 | Fisher et al. |
| 4,861,886 A | 8/1989 | Haga et al. |
| 4,876,260 A | 10/1989 | Fisher et al. |
| 4,981,858 A | 1/1991 | Fisher et al. |
| 5,340,821 A | 8/1994 | Abe et al. |
| 5,571,918 A | 11/1996 | Hayashi et al. |

OTHER PUBLICATIONS

Saunders, et al., "Synthesis and characterization of all four isomers of the muscarinic agonist . . . ", J. Med. Chem., (1987), vol. 30, 969-975.

*Primary Examiner* — Rebecca Anderson

(57) ABSTRACT

An industrially acceptable process for the preparation and purification of cis-2-methylspiro(1,3-oxathiolane-5,3')quiniclidine from a cis/trans mixture of isomers. Treatment of the mixture with an organic sulfonic acid generates a less soluble acid addition salt that is enriched in the cis-isomer. Recrystallization or pulping using various organic solvents allows for enrichment of the cis-isomer by filtration. These new sulfonic acid salts of the cis-isomer of 2-methylspiro(1,3-oxathiolane-5,3')quiniclidine prepared according to the present invention could be further converted into the hydrochloride salt by any known procedures such as treatment with a base and then hydrochloric acid salt formation or exchange of the sulfonic acid salt with hydrochloric acid.

20 Claims, No Drawings

PROCESS FOR THE PREPARATION AND PURIFICATION OF CIS-2-METHYLSPIRO (1,3-OXATHIOLANE-5,3')QUINICLIDINE HYDROCHLORIDE

FIELD OF THE INVENTION

Novel and industrially acceptable processes for the preparation and purification of cis-2-methylspiro(1,3-oxathiolane-5,3')quiniclidine from a cis/trans-mixture of isomers are described. The hydrochloride salt of the cis-isomer of 2-methylspiro(1,3-oxathiolane-5,3')quiniclidine is the active ingredient in Cevimeline Hydrochloride.

BACKGROUND OF THE INVENTION

The present invention refers to a novel, industrially acceptable processes for the preparation and purification of cis-2-methylspiro(1,3-oxathiolane-5,3')quiniclidine, from a cis/trans-mixture of isomers. The hydrochloride salt of the cis-isomer of 2-methylspiro(1,3-oxathiolane-5,3')quiniclidine is the active ingredient in Cevimeline hydrochloride. This pharmaceutical is useful for the treatment of diseases of the central nervous system due to disturbances of central cholinergic function and autoimmune system (Sjörgen's syndrome) and is marketed as Evoxac®

U.S. Pat. No. 4,855,290 teaches a process for the preparation of 2-methylspiro(1,3-oxathiolane-5,3')quiniclidine, wherein the cis-isomer is isolated via fractional recrystallization of its hydrochloric salt. A major disadvantage of this method is the use of repeated (up to 6 times) recrystallizations of the hydrochloride salt of a cis/trans-mixture of 2-methylspiro(1,3-oxathiolane-5,3')quiniclidine. This procedure results in an enriched mother liquor in the cis-isomer that by subsequent chromatographic purification, again undesirable in industrial settings, results in the isolation of the cis-isomer in less than 10% yield. Another drawback of the above procedure is the use of the moisture sensitive and highly reactive boron trifluoride etherate. This reagent is not easy to handle and as such, requires special operations to prevent corroding of the reactors. Also, it should be pointed out that U.S. Pat. No. 4,855,290 uses dichloromethane, an environmentally unfriendly solvent.

U.S. Pat. No. 4,981,858 describes a process for the resolution of the enantiomers of the cis and trans diastereomers of 2-methylspiro(1,3-oxathiolane-5,3')quiniclidine. For example, a racemic sample of the cis or trans diastereomer of 2-methylspiro(1,3-oxathiolane-5,3')quiniclidine is heated with L-tartaric acid in absolute ethanol, followed by fractional recrystallization of the dextrorotatory enantiomer from ethanol. Treatment of the mother liquor with D-tartaric acid allows for isolation of the levorotatory enantiomer. This patent though does not teach any industrially acceptable processes for the preparation and purification of the cis-isomer of 2-methylspiro(1,3-oxathiolane-5,3')quiniclidine.

U.S. Pat. Nos. 5,571,918 and 4,861,886 describe the isomerization of trans-2-methylspiro(1,3-oxathiolane-5,3') quiniclidine to the cis-form in the presence of various acids such as tin tetrachloride. Like boron trifluoride, tin tetrachloride is a very toxic and moisture sensitive chemical, which makes it a hazardous and industrially unfriendly choice, especially when transiting to commercial scale. Also, in terms of delivering pharmaceutical-grade quality Cevimeline hydrochloride (i.e., >99.5% of the cis-isomer), we found that these procedures were either inadequate or too hazardous to be practical.

The lack of industrially advantageous processes for the preparation of the cis-isomer of 2-methylspiro(1,3-oxathiolane-5,3')quiniclidine prompted us to search for novel and industrially acceptable processes for the preparation and purification of the cis-isomer.

Further and other objects of the invention will be realized by those skilled in the art from the following Summary of the Invention and Detailed Description of Preferred Embodiments of the Invention thereof.

SUMMARY OF THE INVENTION

The present invention provides novel processes for the preparation and purification of the cis-isomer of 2-methylspiro(1,3-oxathiolane-5,3')quiniclidine from a cis/trans-mixture of isomers. It was discovered that the cis-isomer of 2-methylspiro(1,3-oxathiolane-5,3')quiniclidine, starting from a cis/trans-mixture (10:1 to 2:1), is selectively converted to a less soluble organic sulfonic acid salt thereby allowing substantial enrichment of the cis-isomer by filtration. Adding to the importance of the above mentioned is the discovery of further purification by recrystallization or pulping using various solvents or a mixture thereof allowing the isolation of pharmaceutically-acceptable cis-2-methylspiro(1,3-oxathiolane-5,3')quiniclidine.

These new sulfonic acid salts of the cis-isomer of 2-methylspiro(1,3-oxathiolane-5,3')quiniclidine prepared according to the present invention could be further converted into the hydrochloride salt by any known procedures such as treatment with a base and then hydrochloric acid salt formation or exchange of the sulfonic acid salt with hydrochloric acid.

According to one embodiment of the present invention there is provided a new process for the preparation and purification of the hydrochloride salt of the cis-isomer of 2-methylspiro(1,3-oxathiolane-5,3')quiniclidine which represents the active ingredient in Cevimeline Hydrochloride. This process is robust and easily scalable to industrial levels.

Other advantages of the present invention include the cost efficiency and simplicity of the process. As well, the Cevimeline hydrochloride produced meets specifications of >99.5% cis-isomer. Further, the Cevimeline hydrochloride is produced with pharmaceutically acceptable residual levels of toluene and organic sulfonic acid and salts thereof, most preferably the camphorsulfonic acid and salts thereof. Pharmaceutically acceptable residual levels for toluene and camphorsulfonic acid and salts thereof vary for specific jurisdictions and would be known by persons skilled in the art.

Further and other advantages of this invention will be appreciated by those skilled in the art.

DESCRIPTION OF PREFERRED EMBODIMENTS OF THE INVENTION

According to one aspect of the invention, a novel process is provided for the preparation and purification of cis-2-methylspiro(1,3-oxathiolane-5,3')quiniclidine from a cis/trans-mixture of isomers. The process is industrially practical, efficient, safe and economical as well as environmentally friendly.

In a preferred embodiment of the invention a cis/trans-mixture of 2-methylspiro(1,3-oxathiolane-5,3')quiniclidine in a cis/trans ratios from 2:1 to 10:1 is dissolved in organic solvent. Examples of suitable organic solvents include C6 to C9 aryl, a C7 to C10 aralkyl, C3 to C6 alkyl ketones, C4 to C8 alkyl ethers, C1 to C6 alkyl alcohols or a mixture thereof. Examples of preferred solvents include toluene, acetone, methyl ethyl ketone, methyl isobutyl ketone, methyl tert-butyl ether, methanol and butanol or a mixture thereof. Most preferably the solvent is toluene or mixture of toluene and methanol (for instance 0.1-3 equiv. of methanol in toluene). A suitable amount of organic sulfonic acid, preferably 0.5 to 2 equivalents relative to the cis-isomer, is added to the mixture at temperatures between 0° and 50° C. Most preferably the acid is methanesulfonic acid, racemic or optically active camphorsulfonic acid, benzenesulfonic acid or para-toluenesulfonic acid. The mixture is stirred for 2 to 48 hours and the precipitate formed is isolated by filtration. The precipitate contains up to 98% of the cis-isomer of 2-methylspiro(1,3-oxathiolane-5,3')quiniclidine as a sulfonic acid salt. Additional purification of the salt by recrystallization or pulping in organic solvents or a mixture thereof at various temperatures allows reaching the high purity levels required for use as an active pharmaceutical. Examples of suitable organic solvents include C5 to C9 alkyl, C6 to C9 aryl, C7 to C10 aralkyl, C4 to C10 alkyl ester, C3 to C6 alkyl ketones, C4 to C8 alkyl ethers, C1 to C6 alkyl alcohols, C1 to C3 carboxylic acids, polyethylene glycols having an average molecular weight of 300-500, or a mixture thereof. Most preferably the solvent is toluene, methyl ethyl ketone, methyl isobutyl ketone, isopropanol, methanol, acetic acids or a mixture thereof. Examples of suitable organic solvents include mixtures of toluene and methanol, acetic acid or polyethylene glycol 400.

The sulfonic acid salts of the cis-isomer of 2-methylspiro (1,3-oxathiolane-5,3')quiniclidine prepared according to the present invention are further converted into the hydrochloride salt by any known procedures such as treatment with a base and then hydrochloric acid salt formation or exchange of the sulfonic acid salt with hydrochloric acid. The hydrochloride salt of the cis-isomer of 2-methylspiro(1,3-oxathiolane-5,3') quiniclidine is the active ingredient in Cevimeline hydrochloride.

The Cevimeline hydrochloride produced according to the present invention meets specifications of >99.5% cis-isomer.

Example I

Preparation of the cis-2-methylspiro(1,3-oxathiolane-5,3')quiniclidin camphorsulfonic acid salt in toluene To a mixture of cis-/trans-2-methylspiro(1,3-oxathiolane-5,3')quiniclidin (5000 mg, 25.1 mmol) containing 70% of the cis-isomer in toluene (25 mL) was added racemic camphorsulfonic acid (3970 mg, 17.09 mmol) and the mixture was stirred for 2 hours at room temperature. The thick precipitate was filtered and the cake washed with toluene to give a 95:5 cis/trans mixture of 2-methylspiro(1,3-oxathiolane-5,3')quiniclidin camphorsulfonic acid salt (6220 mg, 14.4 mmol). $^1$H NMR (400 MHz, CDCl$_3$, cis-isomer): δ=5.16 (q, J=5.9 Hz, 1H); 3.57-3.41 (m, 4H); 3.39-3.30 (m, 2H); 3.27 (d, J=11.2 Hz, 1H); 3.22 (d, J=14.4 Hz, 1H); 3.03 (d, J=11.2 Hz, 1H); 2.83 (d, J=14.4, 1H); 2.61-2.53 (m, 1H); 2.41-2.39 (m, 1H); 2.34-2.27 (m, 1H); 2.21-2.13 (m, 4H); 2.06-1.78 (m, 3H); 1.57 (d, J=5.7 Hz, 3H); 1.42-1.36 (m, 1H); 1.05 (s, 3H); 0.83 (s, 3H).

Example II

Preparation of the cis-2-methylspiro(1,3-oxathiolane-5,3')quiniclidin camphorsulfonic acid salt in toluene To a mixture of cis-/trans-2-methylspiro(1,3-oxathiolane-5,3')quiniclidin (2400 mg, 12.1 mmol) containing 71% of the cis-isomer in toluene (25 mL) was added 1-(S)-camphorsulfonic acid (1960 mg, 8.44 mmol) and the mixture was stirred for 18 hours at room temperature. The precipitate was filtered and the cake washed with toluene to give a 96:4 cis/trans mixture of 2-methylspiro(1,3-oxathiolane-5,3')quiniclidin camphorsulfonic acid salt (1500 mg, 3.4 mmol).

Example III

Preparation of the cis-2-methylspiro(1,3-oxathiolane-5,3')quiniclidin camphorsulfonic acid salt in toluene/methanol To a mixture of cis/trans-2-methylspiro(1,3-oxathiolane-5,3')quiniclidin (23.16 g, 116.38 mmol) containing 77% of the cis-isomer in toluene (250 mL) was added racemic 1-camphorsulfonic acid (20.30 g, 87.20 mmol) followed by methanol (4.70 mL, 116.38 mmol) and the mixture was stirred for 18 hours at room temperature. The precipitate was filtered and the cake washed with toluene to give a 95:5 cis/trans mixture of 2-methylspiro(1,3-oxathiolane-5,3')quiniclidin camphorsulfonic acid salt (37.56 g, 87.14 mmol).

Example IV

Preparation of the cis-2-methylspiro(1,3-oxathiolane-5,3')quiniclidin methanesulfonic acid salt in acetone To a mixture of cis/trans-2-methylspiro(1,3-oxathiolane-5,3')quiniclidin (5000 mg, 25.1 mmol) containing 70% of the cis-isomer in acetone (25 mL) was added methanesulfonic acid (1642 mg, 17.09 mmol) and the mixture was stirred for 2 hours at room temperature. The thick precipitate was filtered and the cake washed with acetone to give a 89:11 cis/trans mixture of 2-methylspiro(1,3-oxathiolane-5,3')quiniclidin methanesulfonic acid salt (4000 mg, 13.6 mmol). $^1$H NMR (400 MHz, CDCl$_3$, cis-isomer): δ=5.16 (q, J=5.9 Hz, 1H); 3.77-3.41 (m, 4H); 3.34-3.25 (m, 3H); 3.06 (d, J=11.3 Hz, 1H); 2.76 (s, 3H); 2.41-2.40 (m, 1H); 2.22-2.16 (m, 2H); 2.14-1.96 (m, 1H); 1.57 (d, J=5.7 Hz, 3H).

Example V

Preparation of the cis-2-methylspiro(1,3-oxathiolane-5,3')quiniclidin benzenesulfonic acid salt in acetone To a mixture of cis/trans-2-methylspiro(1,3-oxathiolane-5,3')quiniclidin (500 mg, 2.5 mmol) containing 75% of the cis-isomer in acetone (2.5 mL) was added benzenesulfonic acid (280 mg, 1.7 mmol) and the mixture was stirred for 36 hours at room temperature. The precipitate was filtered and the cake washed with acetone to give a 90:10 cis/trans mixture of 2-methylspiro(1,3-oxathiolane-5,3')quiniclidin benzenesulfonic acid salt (400 mg). $^1$H NMR (400 MHz, CDCl$_3$, cis-isomer): δ=7.88-7.84 (m, 2H); 7.41-7.36 (m, 3H); 5.11 (q, J=5.6 Hz, 1H); 2.33-2.28 (m, 1H); 1.99-1.86 (m, 2H); 1.83-1.69 (m, 1H); 1.53 (d, J=5.6 Hz, 3H).

Example VI

Preparation of the cis-2-methylspiro(1,3-oxathiolane-5,3')quiniclidin methanesulfonic acid salt in butanol To a mixture of cis/trans-2-methylspiro(1,3-oxathiolane-5,3')quiniclidin (500 mg, 2.5 mmol) containing 70% of the cis-isomer in butanol (2.5 mL) was added methanesulfonic acid (280 mg, 1.7 mmol) and the mixture was stirred for 24 hours at room temperature. Methyl tert-butyl ether (6 mL) was added and the mixture was stirred for 2 hours. The precipitate was filtered and the cake washed with methyl tert-butyl ether to give a 95:5 cis/trans mixture of 2-methylspiro(1,3-oxathiolane-5,3')quiniclidin benzenesulfonic acid salt (300 mg, 1.0 mmol).

Example VII

Recrystallization of the cis-2-methylspiro(1,3-oxathiolane-5,3')quiniclidin camphorsulfonic acid salt in toluene Cis/trans-2-methylspiro(1,3-oxathiolane-5,3')quiniclidin camphor sulfonic acid salt (1480 mg) containing 96% of the cis-isomer in toluene (15 mL) was heated to 90-95° C. for 30 minutes. The heating was stopped and the reaction mixture stirred for 1 hour at room temperature. The precipitate was filtered and the cake washed with toluene to give a 98:2 cis/trans mixture of 2-methylspiro(1,3-oxathiolane-5,3')quiniclidin camphor sulfonic acid salt (1030 mg).

Example VII

Recrystallization of the cis-2-methylspiro(1,3-oxathiolane-5,3')quiniclidin camphorsulfonic acid salt in toluene/methanol Cis/trans-2-methylspiro(1,3-oxathiolane-5,3')quiniclidin camphor sulfonic acid salt (70.0 g) containing 94.6% of the cis-isomer in toluene (350 mL) was heated to 85-90° C. for 30 minutes to complete dissolution. The heating was stopped and methanol (9.72 mL, 0.24 mol, 1.5 equiv.) was added. The reaction mixture was allowed to cool to room temperature and stirred for 3-4 hours. The precipitate was filtered and the cake washed with toluene to give a 98.65:1.35 cis/trans mixture of 2-methylspiro(1,3-oxathiolane-5,3')quiniclidin camphor sulfonic acid salt (51.45 g). This material was suspended in toluene (257 mL) and heated to 85-90° C. to complete dissolution. The heating was stopped and methanol (7.3 mL, 1.5 equiv.) was added. The reaction mixture was allowed to cool to room temperature and stirred for 3-4 hours. The precipitate was filtered and the cake washed with toluene to give a 99.64:0.36 cis/trans mixture of 2-methylspiro(1,3-oxathiolane-5,3')quiniclidin camphor sulfonic acid salt (47.62 g).

Example IX

Recrystallization of the cis-2-methylspiro(1,3-oxathiolane-5,3')quiniclidin camphorsulfonic acid salt in methyl ethyl ketone Cis/trans-2-methylspiro(1,3-oxathiolane-5,3')quiniclidin (2000 mg) camphorsulfonic acid salt containing 94.6% of the cis-isomer in methyl ethyl ketone (10 mL) was heated to 70-75° C. for 15 minutes. The heating was stopped and the reaction mixture stirred for 2 hours at room temperature. The precipitate was filtered and the cake washed with methyl ethyl ketone to give a 98.9:1.1 cis/trans-mixture of 2-methylspiro (1,3-oxathiolane-5,3')quiniclidin camphorsulfonic acid salt (1800 mg).

Example X

Pulping of the cis-2-methylspiro(1,3-oxathiolane-5,3')quiniclidin camphorsulfonic acid salt in toluene Cis/trans-2-methylspiro(1,3-oxathiolane-5,3')quiniclidin (5 g) camphorsulfonic acid salt containing 93.9% of the cis-isomer in toluene (50 mL) was stirred between 20 to 25° C. for 24 hours. The solid was filtered and the cake washed with toluene (10 mL) two times. This gave a 95.2:4.8 cis/trans mixture of 2-methylspiro(1,3-oxathiolane-5,3')quiniclidin camphorsulfonic acid salt (4.8 g).

Example XI

Pulping of the cis-2-methylspiro(1,3-oxathiolane-5,3')quiniclidin camphorsulfonic acid salt in toluene/methanol Cis/trans-2-methylspiro(1,3-oxathiolane-5,3')quiniclidin (10 g) camphorsulfonic acid salt containing 93.9% of the cis-isomer in toluene (50 mL) and methanol (0.743 g) and was stirred between 20 to 25° C. for 24 hours. The solid was filtered and the cake washed with toluene (10 mL) two times. This gave a cis/trans-mixture of 2-methylspiro(1,3-oxathiolane-5,3')quiniclidin camphorsulfonic acid salt (9.1 g, 98.42% cis-isomer). The solid was stirred in toluene (50 mL) and methanol (0.743 g) between 20 to 25° C. for 24 hours. This gave a 99.66:0.34 cis/trans-mixture of 2-methylspiro(1,3-oxathiolane-5,3')quiniclidin camphorsulfonic acid salt (7.7 g).

Example XII

Preparation of the cis-2-methylspiro(1,3-oxathiolane-5,3')quiniclidin hydrochloric acid salt To a solution of cis-2-methylspiro(1,3-oxathiolane-5,3') quiniclidin camphorsulfonic acid salt (1.6 g, 3.71 mmol) in water (30 mL) was added 20 mL of a solution of sodium carbonate to pH=10 at 0-5° C. The aqueous layer was extracted with heptane (3×50 mL). The combined organic layers were dried over sodium sulphate, filtered and evaporated to yield 0.65 g of cis-2-methylspiro(1,3-oxathiolane-5,3')quiniclidin free base as an oil. This material was dissolved in diethyl ether (10 mL), and hydrochloric acid in iso-propanol (20% solution; 0.8 mL; 1.4 equiv.) was added. The mixture was stirred at room temperature for 4 hours. The precipitate was filtered and the cake washed with diethyl ether to give cis-2-methylspiro(1,3-oxathiolane-5,3')quiniclidin hydrochloric acid salt (900 mg, 2.9 mmol, 78% yield). This material contained 91 ppm toluene.

Example XIII

Preparation of the cis-2-methylspiro(1,3-oxathiolane-5,3')quiniclidin hydrochloric acid salt: HCl gas in MTBE and HCl/MTBE solution To a cis-2-methylspiro(1,3-oxathiolane-5,3')quiniclidin camphorsulfonic acid salt (9.9 g, 23.0 mmol) in water (29 mL) was added 2.2 g of 50% sodium hydroxide solution (pH=12) at 0-5° C. The solution was stirred for 15 minutes and extracted with methyl tert-butyl ether (3×60 mL). The combined organic phases were dried over sodium sulphate and filtered through Celite®. The solution was cooled to 0-5° C. and 11.05 g of 8% HCl in methyl tert-butyl ether was added dropwise. The precipitate was filtered and washed with methyl tert-butyl ether (3×20 mL). The cake was dried under vacuum at room temperature to give 5.3 g (22.6 mmol, 98% yield) of Cevimeline hydrochloride. This material contained 17 ppm toluene. $^1$H NMR (400 MHz, CDCl$_3$, cis-isomer): δ=5.19 (q, J=5.6 Hz, 1H); 3.46 (dd, J=2.0 Hz, J=13.7 Hz, 1H); 3.31 (d, J=11.2 Hz, 1H); 3.27-3.15 (m, 6H); 2.27-1.47 (m, 1H); 2.01-1.92 (m, 1H); 1.90-1.82 (m, 2H); 1.77-1.69 (m, 1H); 1.50 (d, J=5.9 Hz, 3H).

PXRD diffractograms were collected on a PANalytical X'Pert Pro MPD diffractometer, using CuK☐ radiation, and an X'Celerator detector (real time multiple strip technology). The generator power settings used were 45 kV and 40 mA. Diffractograms were collected with a step size of 0.017° 2θ and a step size of 11 seconds. Samples were prepared by the back loading technique.

PXRD (peak position +/−0.2° 2θ; peaks listed are at >5% relative intensity): 6.2, 12.4, 14.8, 15.2, 16.0, 16.2, 20.2, 21.6, 22.8, 23.5, 24.1, 24.8, 25.3, 29.2, 31.2, 33.7, 34.9, 37.5, 39.6

Furthermore, as many changes can be made to the invention without departing from the scope of the invention, it is intended that all material contained herein be interpreted as illustrative of the invention and not in a limiting sense.

The invention claimed is:

1. A process for the preparation and purification of the cis-isomer of 2-methylspiro(1,3-oxathiolane-5,3')quiniclidine hydrochloride comprising:
    (a) treatment of a cis/trans mixture of 2-methylspiro(1,3-oxathiolane-5,3')quiniclidine with an organic sulfonic acid in an organic solvent or a mixture thereof;
    (b) purification of the mixture obtained at step (a) by recrystallization or pulping in an organic solvent or a mixture thereof;
    (c) hydrochloric acid salt formation by treatment of the salt obtained at step (b) with hydrochloric acid or treatment with a base and then hydrochloric acid.

2. The process of claim 1 wherein the reaction of cis/trans mixture of 2-methylspiro(1,3-oxathiolane-5,3')quiniclidine at step (a) is performed using methanesulfonic acid, racemic or optically active camphorsulfonic acid, benzenesulfonic acid or p-toluenesulfonic acid.

3. The process of claim 1 wherein the reaction of cis/trans mixture of 2-methylspiro(1,3-oxathiolane-5,3')quiniclidine at step (a) is performed using racemic or optically active camphorsulfonic acid.

4. The process of claim 1 wherein the reaction of cis/trans mixture of 2-methylspiro(1,3-oxathiolane-5,3')quiniclidine at step (a) is performed using racemic camphorsulfonic acid.

5. The process of claim 1 wherein the reaction of cis/trans mixture of 2-methylspiro(1,3-oxathiolane-5,3')quiniclidine with an organic sulfonic acid at step (a) is performed in a solvent selected from the group consisting of: $C_6$ to $C_9$ aryl, a $C_7$ to $C_{10}$ aralkyl, $C_3$ to $C_6$ alkyl ketones, $C_4$ to $C_8$ alkyl ethers, $C_1$ to $C_6$ alkyl alcohols and a mixture thereof.

6. The process of claim 1 wherein the reaction of cis/trans mixture of 2-methylspiro(1,3-oxathiolane-5,3')quiniclidine with an organic sulfonic acid at step (a) is performed in toluene, acetone, methyl ethyl ketone, methyl isobutyl ketone, methyl tert-butyl ether, methanol and butanol or a mixture thereof.

7. The process of claim 1 wherein the reaction of cis/trans mixture of 2-methylspiro(1,3-oxathiolane-5,3')quiniclidine with an organic sulfonic acid at step (a) is performed in toluene.

8. The process of claim 1 wherein the reaction of cis/trans mixture of 2-methylspiro(1,3-oxathiolane-5,3')quiniclidine with an organic sulfonic acid at step (a) is performed in a mixture of toluene and methanol.

9. The process of claim 1 wherein the reaction of cis/trans mixture of 2-methylspiro(1,3-oxathiolane-5,3')quiniclidine at step (a) is performed using racemic or optically active camphorsulfonic acid in toluene.

10. The process of claim 1 wherein the reaction of cis/trans mixture of 2-methylspiro(1,3-oxathiolane-5,3')quiniclidine at step (a) is performed using racemic or optically active camphorsulfonic acid in a mixture of toluene and methanol.

11. The process of claim 1 wherein the purification of cis/trans mixture of 2-methylspiro(1,3-oxathiolane-5,3')quiniclidine obtained at step (a) is performed by recrystallization in an organic solvent or a mixture thereof.

12. The process of claim 1 wherein the purification of cis/trans mixture of 2-methylspiro(1,3-oxathiolane-5,3')quiniclidine obtained at step (a) is performed by recrystallization in an organic solvent selected from the group consisting of: $C_5$ to $C_9$ alkyl, $C_6$ to $C_9$ aryl, $C_7$ to $C_{10}$ aralkyl, $C_4$ to $C_{10}$ alkyl ester, $C_3$ to $C_6$ alkyl ketones, $C_4$ to $C_8$ alkyl ethers, $C_1$ to $C_6$ alkyl alcohols, $C_1$ to $C_3$ carboxylic acids, polyethylene glycols having an average molecular weight of 300-500, and a mixture thereof.

13. The process of claim 1 wherein the purification of cis/trans mixture of 2-methylspiro(1,3-oxathiolane-5,3')quiniclidine obtained at step (a) is performed by recrystallization in toluene, methyl ethyl ketone, methyl isobutyl ketone, methanol, iso-propanol or a mixture thereof.

14. The process of claim 1 wherein the purification of cis/trans mixture of 2-methylspiro(1,3-oxathiolane-5,3')quiniclidine obtained at step (a) is performed by recrystallization in toluene.

15. The process of claim 1 wherein the purification of cis/trans mixture of 2-methylspiro(1,3-oxathiolane-5,3')quiniclidine obtained at step (a) is performed by recrystallization in a mixture of toluene and methanol.

16. The process of claim 1 wherein the purification of cis/trans mixture of 2-methylspiro(1,3-oxathiolane-5,3')quiniclidine obtained at step (a) is performed by pulping in an organic solvent or a mixture thereof.

17. The process of claim 1 wherein the purification of cis/trans mixture of 2-methylspiro(1,3-oxathiolane-5,3')quiniclidine obtained at step (a) is performed by pulping in organic solvents selected from the group consisting of: $C_5$ to $C_9$ alkyl, $C_6$ to $C_9$ aryl, $C_7$ to $C_{10}$ aralkyl, $C_4$ to $C_{10}$ alkyl ester, $C_3$ to $C_6$ alkyl ketones, $C_4$ to $C_8$ alkyl ethers, $C_1$ to $C_6$ alkyl alcohols, $C_1$ to $C_3$ carboxylic acids, polyethylene glycols having an average molecular weight of 300-500, and a mixture thereof.

18. The process of claim 1 wherein the purification of cis/trans mixture of 2-methylspiro(1,3-oxathiolane-5,3')quiniclidine obtained at step (a) is performed by pulping in toluene, methyl ethyl ketone, methyl isobutyl ketone, methanol, iso-propanol or a mixture thereof.

19. The process of claim 1 wherein the purification of cis/trans mixture of 2-methylspiro(1,3-oxathiolane-5,3')quiniclidine obtained at step (a) is performed by pulping in toluene.

20. The process of claim 1 wherein the purification of cis/trans mixture of 2-methylspiro(1,3-oxathiolane-5,3')quiniclidine obtained at step (a) is performed by pulping in a mixture of toluene and methanol.

* * * * *